United States Patent [19]

Calderone et al.

[11] 4,401,583
[45] Aug. 30, 1983

[54] ENHANCING OR AUGMENTING THE AROMA OF DETERGENTS USING 4-METHYL-3-CYCLOHEXENE-1-CARBOXYLIC

[75] Inventors: Nicholas Calderone, Syosset, N.Y.; Hugh Watkins, Lincroft; Takao Yoshida, Long Branch, both of N.J.

[73] Assignee: International Flavors & Fragrances Inc., New York, N.Y.

[21] Appl. No.: 391,587

[22] Filed: Jun. 24, 1982

Related U.S. Application Data

[62] Division of Ser. No. 299,211, Sep. 3, 1981.

[51] Int. Cl.³ ............................................. C11D 3/50
[52] U.S. Cl. .............................. 252/174.11; 252/132; 252/522 R
[58] Field of Search ............... 252/522 R, 174.11, 132; 562/510

[56] References Cited

U.S. PATENT DOCUMENTS

| | | | |
|---|---|---|---|
| 784,411 | 3/1905 | Merling et al. | 562/510 |
| 784,412 | 3/1905 | Merling et al. | 562/510 X |
| 4,113,663 | 9/1978 | Schenk | 252/522 |
| 4,374,123 | 2/1983 | Luccarelli et al. | 424/49 |

OTHER PUBLICATIONS

CA 78:159,061c.
CA 82:P155559f.

*Primary Examiner*—P. E. Willis, Jr.
*Attorney, Agent, or Firm*—Arthur L. Liberman

[57] ABSTRACT

Described in the compound, 4-methyl-3-cyclohexene-1-carboxylic acid having the structure:

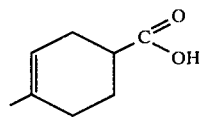

and the use thereof in augmenting or enhancing the aroma of perfume compositions, perfumed articles (e.g., solid or liquid anionic, cationic, nonionic or zwitterionic detergents, fabric softener compositions and fabric softener articles as well as bath preparations and hair preparations). The said 4-methyl-3-cyclohexene-1-carboxylic acid is particularly useful as a replacement for cumin oil and/or cumin aldehyde in perfume compositions, colognes and perfumed articles.

1 Claim, 2 Drawing Figures

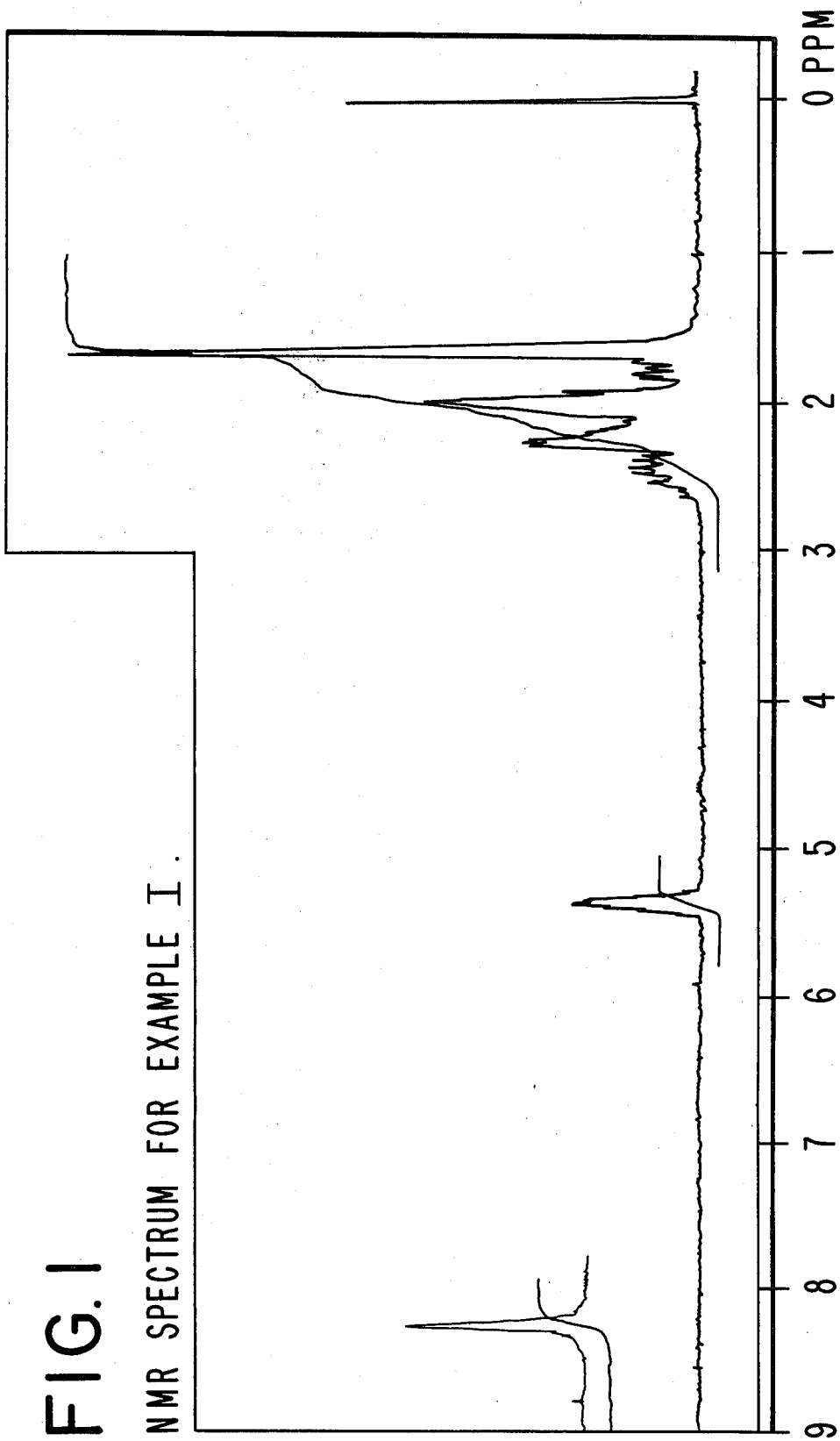

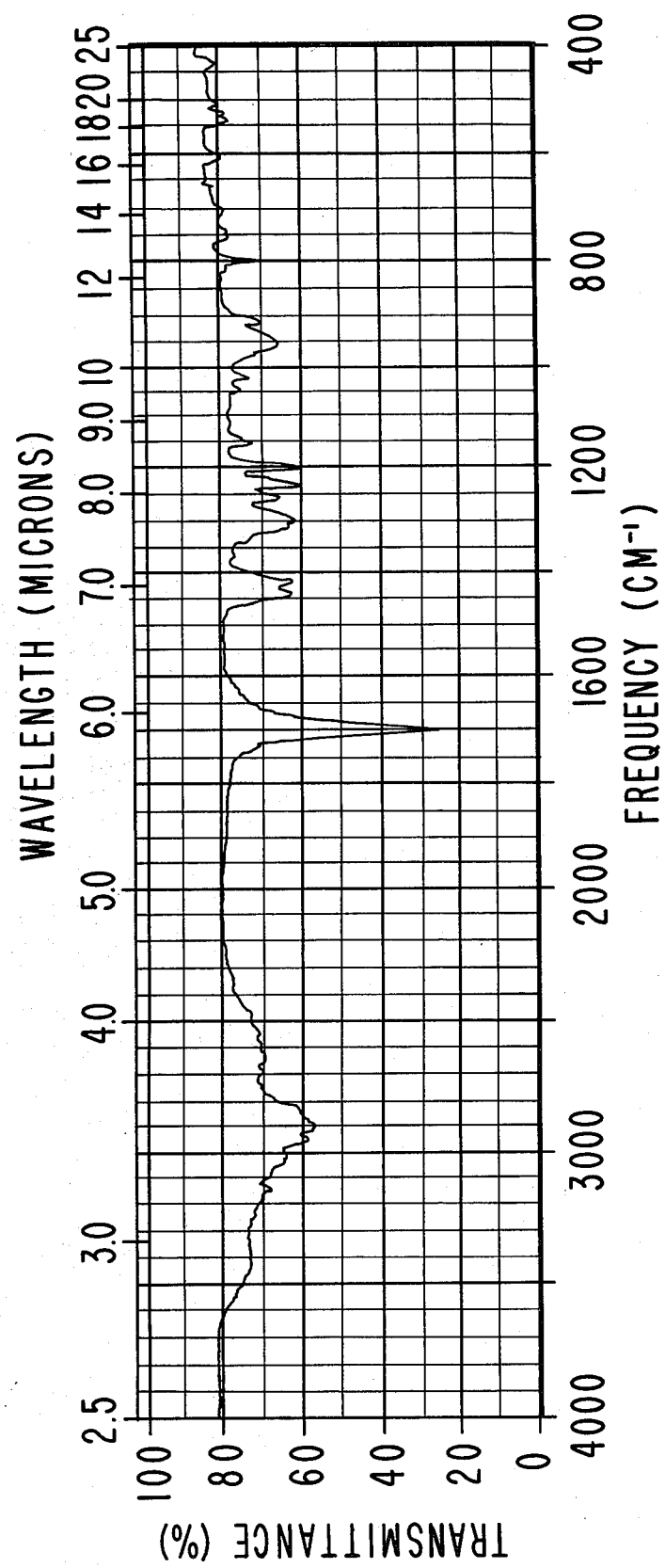

ENHANCING OR AUGMENTING THE AROMA OF DETERGENTS USING 4-METHYL-3-CYCLOHEXENE-1-CARBOXYLIC

This is a divisional of application Ser. No. 299,211, filed Sept. 3, 1981.

BACKGROUND OF THE INVENTION

The instant invention relates to the use in perfumery and particularly in augmenting or enhancing the aroma of perfume compositions, colognes and perfumed articles of the compound, 4-methyl-3-cyclohexene-1-carboxylic acid having the structure:

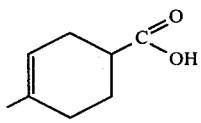

particularly to replace in perfume compositions cumin oil or cumin aldehyde.

As a general rule, cumin oil is used in perfume compositions in trace amounts to introduce green-spicy and green-woody top notes particularly in the woody, floral perfumed types, Oriental bases, mimosa, cassie, and violet. It is also used for "special effects" in modern aldehydic fragrances and for its unusual diffusive power. The oil blends well with lavandin, rosemary, galbanum, oakmoss, bois de rose and the like and it performs well in soaps although it may discolor a white soap tablet visibly after a few months of aging. Cuminaldehyde (p-isopropylbenzaldehyde) occurs to the extent of about 30% in cumin oil and has also been found in traces in the oils of cassie flowers, cinnamon, myrrh and boldo leaf. Its odor recalls orris and it is known in the perfume industry to be useful in preparing synthetic cassie, orris, foin coupe, lilac, lily, mimosa and violet perfumes.

Unfortunately, both cumin oil and cumin aldehyde as well as other constituents of cumin oil, e.g., cymene have been found to cause a considerable degree of irritation to certain perfume wearers in certain climates. Accordingly, a need has arisen for:

(i) A synthetic replacement for cumin oil and/or cumin aldehyde which has no irritency effect in any climate and;

(ii) A replacement for cumin oil which will not discolor soaps.

The use in perfumery of cyclohexene carboxylic acid derivatives is well known. Thus, U.S. Pat. No. 4,113,663 discloses 2-ethyl-6,6-dimethyl-2-cyclohexene-1-carboxylic acid ethyl ester of the formula:

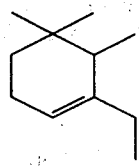

It is indicated in U.S. Pat. No. 4,113,663 that this compound has a particular odor and properties providing an extremely diffuse rose note of very remarkable radiance which is accompanied by honey like, warm and spicy,-fruity,berry like side notes. It is further indicated that the woody, lightly flowery base note with fruity berry like side notes is reminiscent of dried fruits. Disclosed is the intermediate for preparing this ester, the carboxylic acid having the structure:

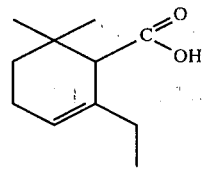

Also described in U.S. Pat. No. 4,113,663 are the following cyclohexene carboxylic acid esters and their organoleptic properties:

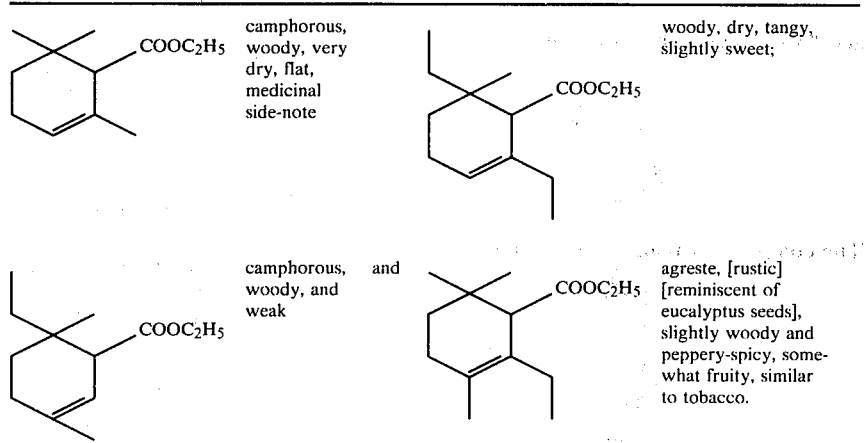

No mention is made in U.S. Pat. No. 4,113,663 of replacement by cyclohexene carboxylic acids of cumin oil or cumin aldehyde.

There has also been determined in the perfume industry to be a need for perfume nuance combinations of cedar like notes with cumin like notes and further with "sweaty" and "leathery" notes.

BRIEF DESCRIPTION OF THE DRAWINGS

FIG. 1 is the NMR spectrum for the reaction product of Example I containing the compound having the structure:

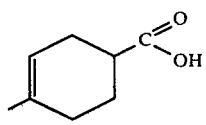

FIG. 2 is the IR spectrum for the reaction product of Example I consisting of the compound having the structure:

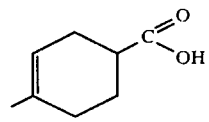

THE INVENTION

The present invention provides the compound having the structure:

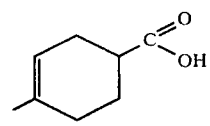

which can exist into forms "endo" having the structure:

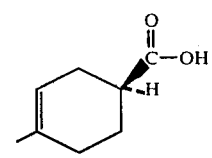

and "exo" having the structure:

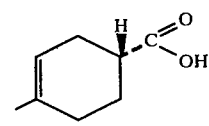

The compound having the structure:

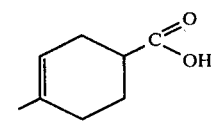

of our invention is capable of augmenting or enhancing sweaty, cuminic aromas with castoreum-like under tones and sweaty, strong cuminic, cedar like aroma nuances on dryout.

The compound having the structure:

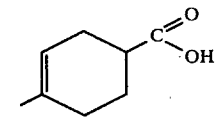

may be prepared by methods well known in the art, e.g., according to the reaction:

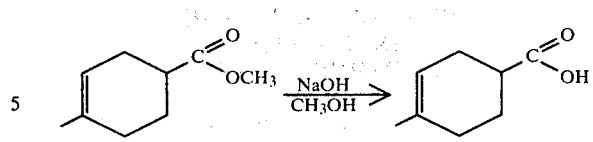

and this preparation is set forth in detail in Example I, infra.

Also contemplated within the scope of this invention are mixtures of the 4-methyl-3-cyclohexene-1-carboxylic acid having the structure:

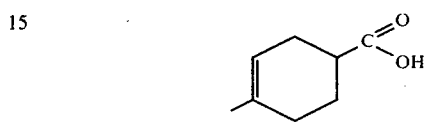

with compounds which yield sweaty, animal, leathery notes defined according to the genera having the structures:

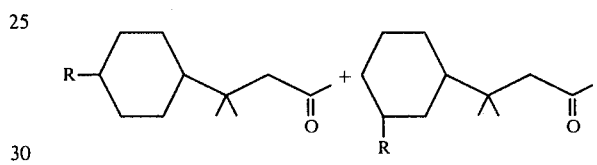

wherein R represents t-butyl or t-amyl as more particularly described in U.S. Pat. No. 3,702,343 issued on Nov. 7, 1972, the disclosure for which is incorporated by reference herein. In addition, the compound of our invention having the structure:

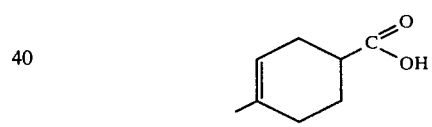

is contemplated to be used in admixture with the cedrol alkyl ethers disclosed in U.S. Pat. No. 3,373,208 issued on Mar. 12, 1968 the disclosure of which is incorporated by reference herein. The cedrol alkyl ethers of U.S. Pat. No. 3,373,208 are defined according to the generic structure:

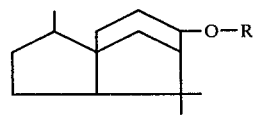

wherein R represents methyl, ethyl, propyl, butyl, allyl or methallyl.

Contemplated within the scope of our invention are mole ratios of 4-methyl-3-cyclohexene-1-carboxylic acid: 2-methyl-2-(t-alkyl cyclohexyl) pentan-4-one:cedrol alkyl ethers of from 1:0:0 to 1:30:0 to 1:1:30 to 1:30:1 to 1:30:0.

Specific 2-methyl-2(tertiary alkyl cyclohexyl) pentan-4-one contemplated within the scope of our invention are those having the structures:

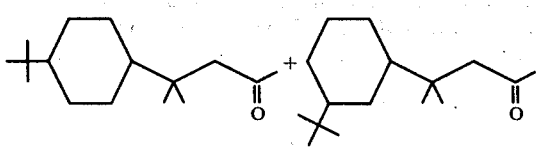

or those having the structures:

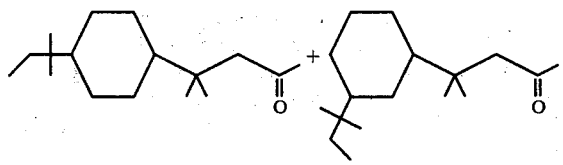

Taken alone the carboxylic acid derivative of our invention having the structure:

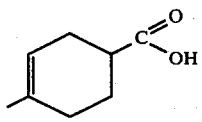

is useful as a cumin replacement and/or as a cumin aldehyde replacement. It is well known in the perfume industry that cumin oil and cumin aldehyde have, under certain conditions, certain irritancy properties with respect to certain wearers.

The carboxylic acid having the structure:

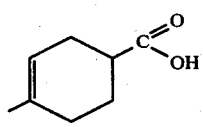

taken alone or taken further together with the pentanone derivatives defined according to the structures:

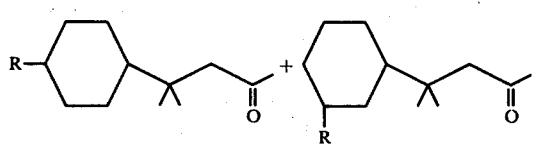

or with cedrol alkyl ether derivatives and one or more auxiliary perfume ingredients including, for example, alcohols, aldehydes, ketones, terpenic hydrocarbons, nitriles, esters other than the esters of our invention, lactones, natural essential oils and synthetic essential oils may be admixed so that the combined odors of the individual components produce a pleasant and desired fragrance, particularly and preferably in those fragrances where cumin oil or cumin aldehyde is necessary such as, cassie fragrances. Such perfume compositions usually contain (a) the main note or the "bouquet" or foundation stone of the composition; (b) modifiers which round off and accompany the main notes; (c) fixatives which include odorous substances which lend a particular note to the perfume throughout all stages of evaporation and substances which retard evaportation; and (d) top notes which are usually low boiling, fresh smelling materials.

In perfume compositions, it is the individual components which contribute to their particular olfactory characteristics, however the overall sensory effect of the perfume composition will be at least the some total of the effect of each of the ingredients. Thus, the carboxylic acid derivative having the structure:

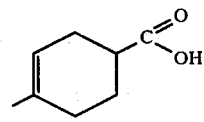

taken alone or taken further together with the pentanone derivatives having the structure:

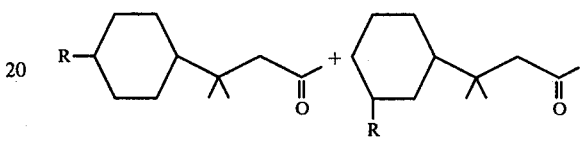

or the cedrol alkyl ethers can be used to alter, modify or enhance the aroma characteristics of a perfume composition, for example, by utilizing or moderating the olfactory reaction contributed by another ingredient in the composition.

The amount of the carboxylic acid derivative having the structure:

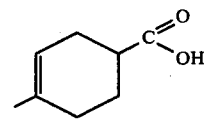

taken alone or taken further together with the pentanone derivatives having the structures:

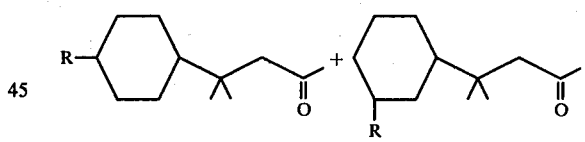

and the cedrol alkyl ether derivatives which will be effective in perfume compositions as well as in perfumed articles (e.g., perfumed polymers, anionic, nonionic, cationic or zwitterionic detergents, soaps, fabric softener compositions, fabric softener articles, bath oils and hair preparations and shampoos) and colognes depends upon many factors including the other ingredients, their amounts and the effects which are desired. It has been found that perfume compositions containing as little as 0.01% of the carboxylic acid derivative having the structure:

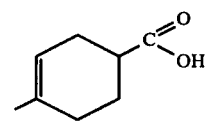

taken alone or taken further together with the pentanone derivatives having the structures:

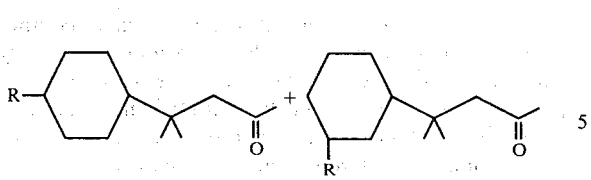

and/or cedrol alkyl ether derivatives, or even less (e.g., 0.005%) can be used to impart, augment or enhance sweaty, cuminic aromas with castoreum under tones with sweaty, cuminic and cedar like top notes and, when the carboxylic acid derivative having the structure:

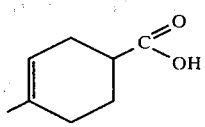

is taken together with the pentanone derivative having the structure:

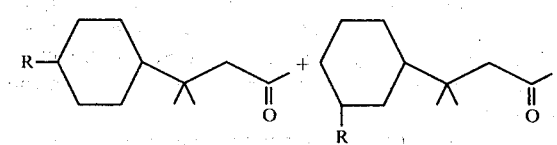

in proportions of from 1:99 up to 99:1, then additional sweaty and leathery and animal like notes are imparted thereto to soaps, cosmetics, anionic, cationic, nonionic, or zwitterionic detergents, fabric softener compositions, fabric softener articles, shampoos, bath preparations and perfumed polymers such as microporous polyacrylic resins or microporous polyethylenes or microporous polypropylenes with or without containing fillers such as talc and mica. The amount employed can range up to 70% of the fragrance components and will depend on considerations of cost, nature of the end product, the effect desired on the finished product and the particular fragrance sought.

The carboxylic acid derivative having the structure:

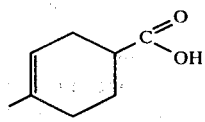

is useful (taken alone or taken together with other ingredients in perfume compositions) as an olfactory component in detergents and soaps, space odorants and deodorants, perfumes, colognes, toilet water, bath preparations such as creams, deodorants, hand lotions and sun screens; powders such as talcs, dusting powder, face powder and the like. When used as an olfactory component as little as 0.05% of the carboxylic acid derivatives having the structure:

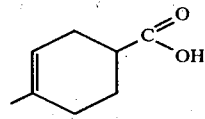

will suffice to impart an intense sweaty, cuminic aroma with castoreum under tones and sweaty, cuminic and cedar aromas on dry out. Generally no more than 6% of the carboxylic acid derivative having the structure:

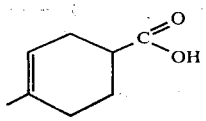

based on the ultimate end product perfumed article is required in the perfumed article composition.

In addition, the perfume composition of fragrance composition of our invention can contain a vehicle or carrier for the carboxylic acid derivative having the structure:

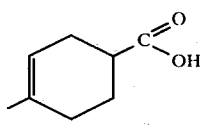

taken alone or further together with the pentanone derivative having the structure:

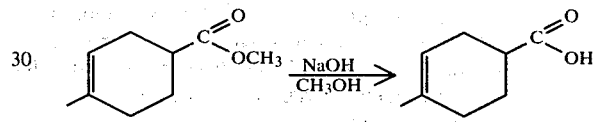

and/or the cedrol alkyl ethers of our invention. The vehicle can be a liquid such as a non-toxic alcohol (e.g., ethyl alcohol), a non-toxic glycol (e.g., 1,2-propylene glycol) or the like. The carrier can also be an absorbent solid such as a gum (e.g., gum arabic or xanthan gum) or components for encapsulating the composition (such as gelatin) as like coacervation or components for encapsulating the composition by means of polymerization of a prepolymer such as the use of the ureaformaldehyde resin.

It will thus be apparent that the carboxylic acid derivative of our invention having the structure:

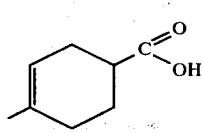

taken alone or taken further together with the pentanone derivatives having the structures:

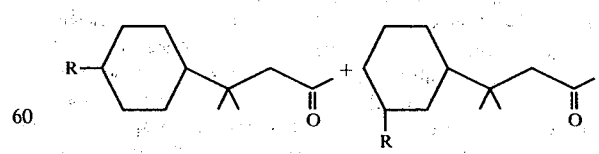

and/or the cedrol alkyl ether derivatives can be utilized to alter, modify or enhance sensory properties particularly organoleptic properties in a wide variety of consumable materials.

The following examples serve to illustrate our invention but our invention is only intended to be limited as indicated in the appended claims. All parts and percentages given herein are by weight unless otherwise specified.

EXAMPLE I

PREPARATION OF 4-METHYL-3-CYCLOHEXENE-1-CARBOXYLIC ACID REACTION

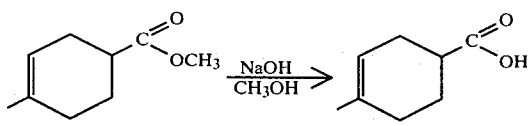

Into 1 liter reaction flask equipped with stirrer, thermometer reflux condenser and heating mantle is placed 100 ml anhydrous methyl 1.25 moles (100 grams) of 50% aqueous NaOH solution, 100 ml water and 154 grams (1 mole) of the methyl ester of 4-methyl-cyclohexene-1-carboxylic acid. The reaction mass is stirred for a period of 5 hours at room temperature and then extracted with 1 volume of diethyl ether. The aqueous layer is set aside with 10% hydrochloric acid and extracted with diethyl ether. The diethyl ether extracts are washed with saturated sodium chloride solution and the ether is evaporated yielding 100.5 grams of solid melting at 95° C. This material is the carboxylic acid having the structure:

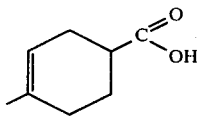

as confirmed by NMR and IR analysis.

FIG. 1 sets forth the NMR spectrum for this compound.

FIG. 2 sets forth the IR spectrum for this compound.

The resulting compound has a sweaty cuminic aroma with castoreum under tones (fresh) and a sweaty cuminic cedar like aroma on dry out.

EXAMPLE II

| CASSIE PERFUME COMPOSITION: | |
|---|---|
| Ingredient | Parts by Weight |
| Linalool | 40 |
| 4-Methyl-3-cyclohexene-1-carboxylic acid prepared according to Example I | 10 |
| Terpineol | 150 |
| Methyl heptenyl carbonate | 10 |
| Orris Concrete | 20 |
| Methyl ionone | 300 |
| Mimosa absolute | 50 |
| Eugenol | 100 |
| Anisic aldehyde | 70 |
| Orange flower absolute | 10 |
| Cassie absolute | 10 |
| Methyl naphthyl ketone | 50 |
| Hydroxy citronellal | 150 |
| n-Decyl aldehyde (10% in diethyl phthalate) | 10 |

The 4-methyl-3-cyclohexene-1-carboxylic acid is an excellent replacer for the cuminic aldehyde. In fact, the 4-methyl-3-cyclohexene-1-carboxylic acid imparts a more "natural" character to this cassie fragrance formulation.

EXAMPLE III

CHYPRE ESSENCE

The following Chypre essence composition is prepared:

| Ingredients | Parts by Weight |
|---|---|
| Santalol | 60 |
| Coumarin | 70 |
| Musk ketone | 30 |
| Musk ambrette | 20 |
| Ambreine absolute | 25 |
| Tarragon oil | 25 |
| Angelica root oil | 5 |
| Clary sage | 30 |
| Vetivert oil | 60 |
| Linalool | 30 |
| Patchouli oil | 20 |
| Iso-eugenol | 35 |
| Methyl ionone | 50 |
| Oakmoss absolute | 60 |
| Bergamot oil | 225 |
| Jasmin absolute | 20 |
| Rose absolute | 15 |
| Methyl salicylate | 2 |
| Lavender oil | 3 |
| Vanillin | 15 |
| Heliotropin | 35 |
| Ylang oil, Manila | 70 |
| Cinnamyl acetate | 25 |
| Benzoil resinoid | 50 |
| 2-methyl-2-(4'-t-butyl cyclohexyl) pentan-4-one prepared according to the process of Example II of U.S. Pat. No. 3,702,343 incorporated by reference herein) | 20 |
| 4-methyl-3-cyclohexene-1-carboxylic acid prepared according to Example I, supra | 20 |

The original mixture without the 2-methyl-2-(4'-t-butyl cyclohexyl) pentan-4-one and without the 4-methyl-3-cyclohexene-1-carboxylic acid was designed as a chypre essence. The addition of the pentan-4-one compound taken together with the 4-methyl-3-cyclohexene-1-carboxylic acid and the quantities given increases (a) the intensity of the essence; (b) the diffusion of the fragrance; (c) adds certain "natural sweaty, leathery, cuminic animal like cuminic cedar like and castoreum like aroma nuances".

EXAMPLE IV

The following mixture is prepared:

| Ingredients | Parts by Weight |
|---|---|
| Bergamot oil CP | 100 |
| Orange oil Fla. CP | 100 |
| Bitter orange oil WI | 50 |
| Lemon oil Cal. CP | 20 |
| Mandarin oil | 20 |
| Lime oil exp. WI | 10 |
| Ocimene | 10 |
| Ortho tertiary butyl cyclohexanyl acetate | 10 |
| Cedryl methyl ether | 50 |
| 4-methyl-3-cyclohexene-1-carboxylic acid | 50 |

The mixture of cedryl methyl ether and 4-methyl-3-cyclohexene-1-carboxylic acid imparts to this woody amber fragrance an intense cedar, cumin like, castoreum like aroma nuance. When the pentanone derivative having the structure:

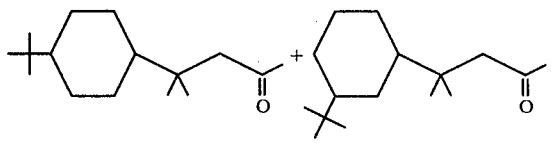

is added in the amount of 20 parts by weight to this mixture. The resulting mixture in addition, has pleasant animal, leathery and sweaty aroma under tones.

EXAMPLE V

PREPARATION OF COSMETIC POWDER COMPOSITIONS

Cosmetic powder compositions are prepared by mixing in a ball mill 100 grams of talcum powder with 0.25 grams of each of the substances set forth in Table I below. Each of the cosmetic powder compositions has an excellent aroma as described in Table I below:

TABLE I

| Substance | Aroma Description |
|---|---|
| 4-Methyl-3-cyclohexene-1-carboxylic acid | Sweaty, cuminic aroma with castoreum under tones (fresh) with sweaty, strong cuminic cedar like aroma nuances on dryout. |
| The fragrance formulation of Example II. | A strong cassie aroma with cuminic sweaty notes and castoreum cedar like undertones. |
| The fragrance formulation of Example III. | A chypre aroma with sweaty, leathery, animal like cuminic like castoreum like and cedar wood undertones. |
| The fragrance formulation of Example IV. | A strong cedar aroma with intense woody, amber nuances and cuminic castoreum like undertones. |

EXAMPLE VI

PERFUMED LIQUID DETERGENTS

Concentrated liquid detergents (Lysine salt of n-dodecylbenzene sulfonic acid as more specifically described in U.S. Pat. No. 3,948,818, issued on April 6, 1976 incorporated by reference herein) with aroma nuances as set forth in Table I of Example V, are prepared containing 0.10%, 0.15%, 0.20%, 0.25%, 0.30% and 0.35% of the substance set forth in Table I of Example V. They are prepared by adding and homogeneously mixing the appropriate quantity of substance set forth in Table I of Example V in the liquid detergent. The detergents all possess excellent aromas as set forth in Table I of Example V, the intensity increasing with greater concentrations of substance as set forth in Table I of Example V.

EXAMPLE VII

PREPARATION OF COLOGNES AND HANDKERCHIEF PERFUMES

Compositions as set forth in Table I of Example V are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example V are imparted to the colognes and to the handkerchief perfumes at all levels indicated.

EXAMPLE VIII

PREPARATION OF SOAP COMPOSITIONS

One hundred grams of soap chips [per sample] (IVORY ®, produced by the Procter & Gamble Company of Cincinnati, Ohio), are each mixed with one gram samples of substances as set forth in Table I of Exaple V until homogenous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table I of Example V.

EXAMPLE IX

PREPARATION OF SOLID DETERGENT COMPOSITIONS

Detergents are prepared using the following ingredients according to Example I of Canadian Pat. No. 1,007,948 (incorporated by reference herein):

| Ingredient | Percent by Weight |
|---|---|
| "Neodol ® 45-11 (a $C_{14}$-$C_{15}$ alcohol ethoxylanted with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table I of Example V. Each of the detergent samples has an excellent aroma as indicated in Table I of Example V.

EXAMPLE X

Utilizing the procedure of Example I at column 15 of U.S. Pat. No. 3,632,396 (the disclosure of which is incorporated herein by reference), nonwoven cloth substrates useful as dried-added fabric softening articles of manufacture are prepared wherein the substrate, the substrate coating, the outer coating and ther perfuming material are as follows:

1. A water "dissolvable" paper ("Dissolvo Paper")
2. Adogen 448 (m.p. about 140° F.) as the substrate coating; and
3. An outer coating having the following formulation (m.p. about 150° F.):
    57% $C_{20\text{-}22}$ HAPS
    22% isopropyl alcohol
    20% antistatic agent
    1% of one of the substances as set forth in Table I of Example V.

Fabric softening compositions prepared according to Example I at column 15 of U.S. Pat. No. 3,632,396 having aroma characteristics as set forth in Table I of Example V, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table I of Example V is admixed in each case with the outer casing mixture, thereby providing a total aromatized outer coating weight ratio to substrate of about 0.5:1 by weight of the substrate. The aroma characteristics are imparted in a pleasant manner to the head space in a dryer on operation thereof in each case using said dryer-added fabric softener non-woven fabrics and these aroma characteristics are described in Table I of Example V, supra.

EXAMPLE XI

HAIR SPRAY FORMULATIONS

The following hair spray formulation is prepared by first dissolving PVP/VA E-735 copolymer manufactured by the GAF Corporation of 140 West 51st Street, New York, New York, in 91.62 grams of 95% food grade ethanol. 8.0 grams of the polymer is dissolved in the alcohol. The following ingredients are added to the PVP/VA alcoholic solution:

| | |
|---|---|
| Dioctyl sebacate | 0.05 weight percent |
| Benzyl alcohol | 0.10 weight percent |
| Dow Corning 473 fluid (prepared by the Dow Corning Corporation) | 0.10 weight percent |
| Tween 20 surfactant (prepared by ICI America Corporation) | 0.03 weight percent |
| One of the perfumery substances as set forth in Table I of Example V, supra | 0.10 weight percent |

The perfuming substances as set forth in Table I of Example V add aroma characteristics as set forth in Table I of Example V which are rather intense and aesthetically pleasing to the users of the soft-feel, good-hold pump hair sprays.

EXAMPLE XII

CONDITIONING SHAMPOOS

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "COMPOSITION A".

Gafquat ® 755 N polymer (manufactured by GAF Corporation of 140 West 51st Street, New York, New York) (5.0 weight percent) is admixed with 0.1 weight percent sodium sulfate and 1.4 weight percent polyethylene glycol 6000 distearate produced by Armak Corporation. This material is "COMPOSITION B".

The resulting COMPOSITION A & COMPOSITION B are then mixed in a 50:50 wt ratio of A:B and cooled to 45° C. and 0.3 wt percent of perfuming substance as set forth in Table I of Example V is added to the mixture. The resulting mixture is cooled to 40° C. and blending is carried out for an additional one hour in each case. At the end of this blending period, the resulting material has a pleasant fragrance as indicated in Table I of Example V.

What is claimed is:

1. A process for augmenting or enhancing the aroma of a solid or liquid anionic, cationic, nonionic or zwitterionic detergent comprising the step of adding to a solid or liquid anionic, cationic, nonionic or zwitterionic detergent base, an aroma augmenting or enhancing quantity of 4-methyl-3-cyclohexene-1-carboxylic acid defined according to the structure:

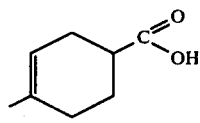

* * * * *